March 23, 1976 R. KORDES Plant Pat. 3,846
ROSE PLANT
Filed Dec. 18, 1974
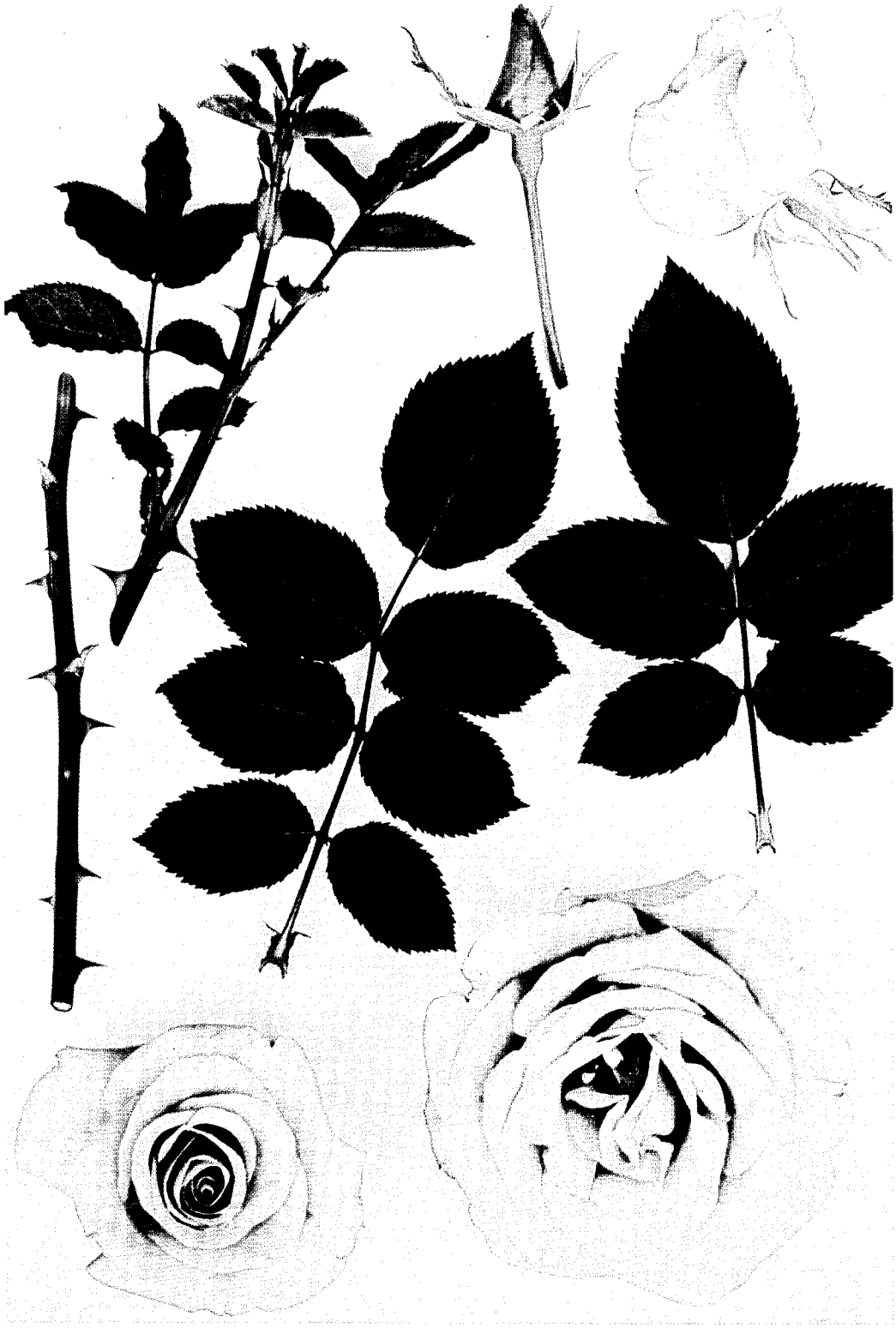

United States Patent

Plant Pat. 3,846

Patented Mar. 23, 1976

1

3,846

ROSE PLANT

Reimer Kordes, Sparrieshoop, near Elmshorn in Holstein, Germany, assignor to Jackson & Perkins Company, Medford, Oreg.

Filed Dec. 18, 1974, Ser. No. 533,804

Int. Cl. A01h 5/00

U.S. Cl. Plt.—27 1 Claim

This invention relates to a new and distinct cultivar of rose plant of the floribunda class originated by me by crossing the cultivar Zorina, U.S. Plant Pat. 2,321, by the cultivar Silver Star, unpatented.

The primary objective of this breeding was to produce a new and improved cultivar of the floribunda class bearing flowers similar in form and size to Zorina but of a lavender or lilac color.

This objective was fully achieved along with other desirable improvements as evidenced by the following unique combination of characteristics which are outstanding in the new cultivar and which distinguish it from its parents as well as from all other cultivars of which I am aware:

1. Bushy, well branched, vigorous plant of truly floribunda form.
2. Abundant large, leathery foliage.
3. Broad base, pointed bud of a magenta-lilac hue.
4. Imbricated high centered open flowers of a lighter shade of magenta-lilac.
5. Strong fragrance.

Asexual reproduction of this new cultivar by budding, as performed at Sparrieshoop, W. Germany, shows that the aforementioned characteristics come true to form and are established and transmitted through succeeding propagations.

The accompanying illustrations show typical specimens of the vegetative growth and flowers of this new cultivar in different stages of development and as depicted in color as nearly true as it is reasonably possible to make the same in a color illustration of this character.

The following is a detailed description of my new rose cultivar with color terminology in accordance with *Hickethier* on Wilson's horticultural color chart (W) except where ordinary dictionary significance of color is indicated.

Parentage: Seedling.
- *Seed parent.*—Seedling of Zorina, U.S. Plant Pat. 2,321.
- *Pollen parent.*—Silver Star.

Classification:
- *Botanical.*—Rosa hybrid.
- *Commercial.*—Floribunda.

FLOWER

Observations were made at Sparrieshoop, West Germany, on July 9, 1974 from plants grown in greenhouse.

Blooming habit: Recurrent, continuous.

Bud:
- *Size.*—4 cm. when petals start to unfurl.
- *Form.*—Very long, pointed.
- *Color.*—When sepals first divide—near Magenta-lilac Hickethier (393) to (493). When half blown; upper side of petals Magenta-lilac Hickethier (243); lower side of petals Hickethier (363) with light-yellow base Hickethier (200).
- *Sepals.*—Color: Outer surface near Hickethier (613). Inner surface near Hickethier (302). Three appendaged sepals lightly appendaged. Two unappendaged sepals hairy edged.

2

- *Receptacle.*—Color: Hickethier (603). Shape: Pear. Size: Large, long. Surface: Smooth.
- *Peduncle.*—Length: Long. Surface: Smooth. Color: Medium green. Strength: Stiff, erect, heavy.
- *Opening.*—Petals fold out in spiral manner.

Bloom:
- *Size.*—Large. Average size when fully expanded 9 cm.
- *Borne.*—Several together.
- *Stems.*—Long, strong.
- *Form.*—When first open, high centered. Permanence—retains its form to the end; outer petal edges slightly curled.
- *Petalage.*—Number of petals under normal conditions 28.
- *Color.*—Center of flower: Upper side of petals Spinel Pink (0625W). Reverse side of petals same. Base of petals point light-yellow, Hickethier (300). General tonality from a distance Spinel Pink (0625W).
- *Discoloration.*—General tonality at end of first day—Spinel Pink (0625W). Third day—Spinel Pink (0625/2/W).

Petals:
- *Texture.*—Thick.
- *Shape.*—Oval.
- *Form.*—Edges slightly quilled.
- *Arrangement.*—Imbricated. Petaloids in center—few.
- *Persistence.*—Drop off cleanly.
- *Fragrance.*—Strong.
- *Lastingness.*—On the plant—long. As cut flower—very long.

Reproductive parts:
- *Stamens, anthers.*—Medium, many. Color—white, yellow. Arrangement—regular around styles.
- *Filaments (threads).*—Color—reddish.
- *Pollen.*—Lemon yellow.
- *Styles.*—Color—mostly white.
- *Stigmas.*—Color—white.

PLANT

Form: Bush.

Growth: Vigorous, upright, branching.

Foliage:
- *Size.*—Large.
- *Quantity.*—Normal.
- *Color.*—New foliage: Garnet Brown Hickethier (894) to (845). Old foliage: Near Spinach Hickethier (839).
- *Shape.*—Oval.
- *Texture.*—Leathery.
- *Edge.*—Serrated.
- *Serration.*—Single, small.
- *Petiole (rachis).*—Color—green. Underside—prickles.
- *Stipules.*—Long, bearded.
- *Disease resistance.*—Resistant to mildew, blackspot, under normal growing conditions at 2201 Sparrieshoop, West Germany in greenhouse.

Wood:
- *New wood.*—Color—Bronzy brown. Bark—smooth.
- *Old wood.*—Color—Green. Bark—smooth.

Prickles:
- *Quantity.*—On main stalks from base—few. On laterals from stalk—few.
- *Form.*—Narrow based, medium, hooked downwardly.
- *Color when young.*—Brown.
- *Position.*—Irregular.

Small prickles:

*Quantity.*—On main stalks—few. On laterals—few.
*Color.*—Green.

I claim:

1. A new and distinct cultivar of rose plant of the floribunda class, substantially as herein shown and described, characterized particularly as to novelty by the unique combination of its pointed, broad based bud of magenta-lilac, an abundance of large, leathery, foliage, well branched habit of growth, long stem length of its cut flowers, high centered imbricated form of blooms, a petal count of about 28, and strong fragrance.

No references cited.

ROBERT E. BAGWILL, Primary Examiner